United States Patent
Noda et al.

(10) Patent No.: US 6,224,212 B1
(45) Date of Patent: May 1, 2001

(54) FUNDUS MEASURING APPARATUS AND RECORDING MEDIUM WITH FUNDUS MEASUREMENT PROGRAM RECORDED THEREON

(75) Inventors: Manabu Noda; Norimasa Hayashi, both of Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/429,025

(22) Filed: Oct. 29, 1999

(30) Foreign Application Priority Data

Oct. 29, 1998 (JP) .................................................. 10-308134

(51) Int. Cl.⁷ ...................................................... A61B 3/14
(52) U.S. Cl. ................................................................ 351/206
(58) Field of Search .................................... 351/205, 206, 351/208, 211, 221

(56) References Cited

U.S. PATENT DOCUMENTS

| 4,715,703 | 12/1987 | Cornsweet et al. ................... 351/205 |
| 5,315,329 | * 5/1994 | McAdams ............................. 351/206 |
| 5,353,073 | * 10/1994 | Kobayashi ............................ 351/221 |

FOREIGN PATENT DOCUMENTS

| 2700654 | 7/1994 | (FR) .............................. H04N/15/00 |
| 7-136121 | 5/1995 | (JP) ................................. A61B/3/12 |
| 7-255681 | 10/1995 | (JP) ................................. A61B/3/14 |
| 8-567 | 1/1996 | (JP) ................................. A61B/3/14 |

OTHER PUBLICATIONS

Patent Abstracts of Japan vol. 1996, No. 05, May 31, 1996 (1996–05–31) & JP 08 000567 A (Asahi Koyo KK), Jan. 9, 1996 (1996–01–09) *Abstract*.

Ramirez M et al: "3–D Digital Surface Recovery of the Optic Nerve Head from Stereo Fundus Images", Proceedings of the Annual Symposium on Computer Based Medical Systems, US, New York, IEEE. D, vol. Symp. 5, pp. 284–291 XP000282958ISBN: 0–8186–2742–5 Whole Document.

* cited by examiner

Primary Examiner—George Manuel
(74) Attorney, Agent, or Firm—Sughrue, Mion, Zinn Macpeak & Seas, PLLC

(57) ABSTRACT

A fundus measuring apparatus which measures a three-dimensional configuration of a fundus on the basis of stereoscopic images of the fundus. With respect to a left image and a right image of inputted stereoscopic images of the fundus, integration data is obtained by integrating density information concerning at least one direction of its vertical direction and horizontal direction. Parallax information is measured on the basis of differential data obtained by further differentiating the integral data. The height of each portion of the fundus is determined from left and right images extracted from the stereoscopic images of the fundus on the basis of this parallax information, so as to generate a three-dimensional configuration of the fundus.

22 Claims, 4 Drawing Sheets

FUNDUS MEASURING APPARATUS AND RECORDING MEDIUM WITH FUNDUS MEASUREMENT PROGRAM RECORDED THEREON

BACKGROUND OF THE INVENTION

The present invention relates to a fundus measuring apparatus for measuring a three-dimensional configuration of the fundus (fundus) on the basis of stereoscopic images of the fundus as well as a recording medium with a fundus measurement program recorded thereon.

It is said that the observation of the optic disc (hereafter simply referred to as the disc) through an image of the fundus is important as the diagnosis of glaucoma which is known as one of disorders in the visual function. In recent years, apparatuses have been proposed in which a three-dimensional configuration of the fundus is measured on the basis of stereoscopic images of the fundus photographed by a stereoscopic fundus camera, and the cup of the disc and a peripheral portion of the disc are analyzed quantitatively.

The method of measuring the three-dimensional information of the fundus on the basis of stereoscopic images of the fundus is generally known as a stereoscopic matching method, and in obtaining height information it is important to extract corresponding spots (corresponding points) in left and right images. To accurately effect the extraction of corresponding spots, it is necessary to determine an amount of deviation (hereafter referred to as the parallax) of the overall image due to an refractive error of the photographed eye, to thereby cause the left image and the right image to correspond to each other. Conventionally, the parallax is determined on the basis of a characteristic point such as a branching point of a blood vessel or the like on the fundus to cause the left and right images to correspond to each other.

However, there are cases where the contrast in the photographed stereoscopic images of the fundus is not good, and if a branching point of the blood vessel is unclear, the accuracy in correspondence between the left and right images is often poor, often making the measurement impossible. In addition, since the measurement of the parallax based on the branching point of the blood vessel relies on two-dimensional measurement, there has been a problem in that a long processing time is required.

Still further, the extraction of corresponding spots from the left and right images causes a problem in which the overall processing time is long, since to search for pixels (region) which are best in conformity with specific pixels (specific region) of one image, the other image must be searched minutely over a certain range.

SUMMARY OF THE INVENTION

In view of the above-described problems, an object of the present invention is to provide a fundus measuring apparatus and a recording medium with a fundus measurement program recorded thereon, which are capable of accurately measuring the three-dimensional configuration of the fundus on the basis of stereoscopic images of the fundus in a short processing time.

The present invention provides the followings:

(1) A fundus measuring apparatus for measuring a three-dimensional configuration of a fundus on the basis of a stereoscopic image of the fundus, the apparatus comprising:

input means for inputting the stereoscopic image of the fundus;

image extracting means for extracting left and right images from the stereoscopic image of the fundus thus inputted by the input means; and three-dimensional configuration generating means for generating a three-dimensional configuration of the fundus on the basis of the left and right images thus extracted by the image extracting means.

(2) The fundus measuring apparatus according to (1), wherein the image extracting means includes:

integration means for integrating horizontal and vertical density information on the stereoscopic image of the fundus thus inputted by the image input means to obtain integral values;

threshold setting means for setting at least one threshold for the integral values thus obtained by the integration means; and background separating means for separating the left and right images from a background using coordinates obtained on the basis of the integral values and the at least one threshold value thus set by the threshold setting means.

(3) The fundus measuring apparatus according to (1), wherein the image extracting means includes:

integration means for integrating at least one of horizontal and vertical density information on the stereoscopic image of the fundus thus inputted by the image input means to obtain integral data;

differential means for differentiating the integral data thus obtained by integration means to obtain differential data; and parallax measuring means for obtaining a parallax on the basis of the differential data thus obtained by the differential means.

(4) The fundus measuring apparatus according to (3), wherein the parallax measuring means obtains the parallax on the basis of maximum cross correlation values of the differential data obtained by the differential means.

(5) The fundus measuring apparatus according to (1), wherein the image extracting means includes image separating means for excluding an image region which does not exist commonly on the left and right images.

(6) The fundus measuring apparatus according to (1) further comprising:

corresponding spots extracting means for generating multiple-resolution images whose resolutions are consecutively lowered with respect to the left and right images extracted by the image extracting means, and extracting corresponding spots from the left and right images using the multiple-resolution images in order starting from the lowest one of the multiple-resolution images; and wherein the three-dimensional configuration generating means generates the three-dimensional configuration of the fundus on the basis of the corresponding spots thus obtained.

(7) The fundus measuring apparatus according to (1), wherein the image input means is equipped with a fundus camera for photographing the stereoscopic image of the fundus.

(8) The fundus measuring apparatus according to (1) further comprising:

output means for visually outputting the three-dimensional configuration of the fundus thus generated by the three-dimensional image generating means.

(9) A recording medium storing therein a program that is to be executed by an operating and analyzing unit to measure a three-dimensional configuration of a fundus on the basis of a stereoscopic image of the fundus, the program comprising:

an image extracting step of extracting left and right images from an inputted stereoscopic image of a fundus; and a three-dimensional-configuration generating step of generating a three-dimensional configuration of the fundus on the basis of the left and right images thus extracted.

(10) The recording medium according to (9), wherein the image extracting step includes the steps of:

integrating horizontal and vertical density information on the inputted stereoscopic image of the fundus to obtain integral values;

setting at least one threshold for the integral values thus obtained by the integrating step; and separating the left and right images from a background using coordinates obtained on the basis of the integral values and the at least one threshold value thus set by the setting step.

(11) The recording medium according to (9), wherein the image extracting step includes the steps of:

integrating at least one of horizontal and vertical density information on the inputted stereoscopic image of the fundus to obtain integral data;

differentiating the integral data thus obtained by integrating step to obtain differential data; and obtaining a parallax on the basis of the differential data thus obtained by the differential step.

(12) The recording medium according to (9), wherein the image extracting step includes an image separating step of excluding an image region which does not exist commonly on the left and right images.

(13) The recording medium according to (9), wherein the program further comprises:

a corresponding spots extracting step of generating multiple-resolution images whose resolutions are consecutively lowered with respect to the left and right images extracted by the image extracting step, and extracting corresponding spots from the left and right images using the multiple-resolution images in order starting from the lowest one of the multiple-resolution images; and wherein the three-dimensional configuration generating step generates the three-dimensional configuration of the fundus on the basis of the corresponding spots thus obtained.

(14) A fundus measuring apparatus for measuring a three-dimensional configuration of a fundus on the basis of a stereoscopic image of the fundus, the apparatus having an operating and analyzing unit storing therein a fundus measuring program to execute the following steps of:

integrating at least one of horizontal and vertical density information on an inputted stereoscopic image of a fundus to obtain integral data;

differentiating the integral data thus obtained by integrating step to obtain differential data;

obtaining a parallax on the basis of the differential data thus obtained by the differential step;

extracting left and right images from the stereoscopic image on the basis of the parallax; and obtaining a height of each part of the fundus on the basis of the left and right images thus extracted, thereby generating a three-dimensional configuration of the fundus.

(15) A fundus measuring apparatus for measuring a three-dimensional configuration of a fundus on the basis of a stereoscopic image of the fundus, the apparatus having an operating and analyzing unit storing therein a fundus measuring program to execute the following steps of:

extracting left and right images from an inputted stereoscopic image of a fundus;

generating multiple-resolution images whose resolutions are consecutively lowered with respect to the left and right images thus extracted, and extracting corresponding spots from the right and left images using the multiple-resolution images in order starting from the lowest one of the multiple-resolution images; and generating a three-dimensional configuration of the fundus on the basis of the corresponding spots thus obtained.

The present disclosure relates to the subject matter contained in Japanese patent application No. Hei. 10-308134 (filed on Oct. 29, 1998), which is expressly incorporated herein by reference in its entirety.

DESCRIPTION OF THE PREFERRED EMBODIMENT

Figure 1:
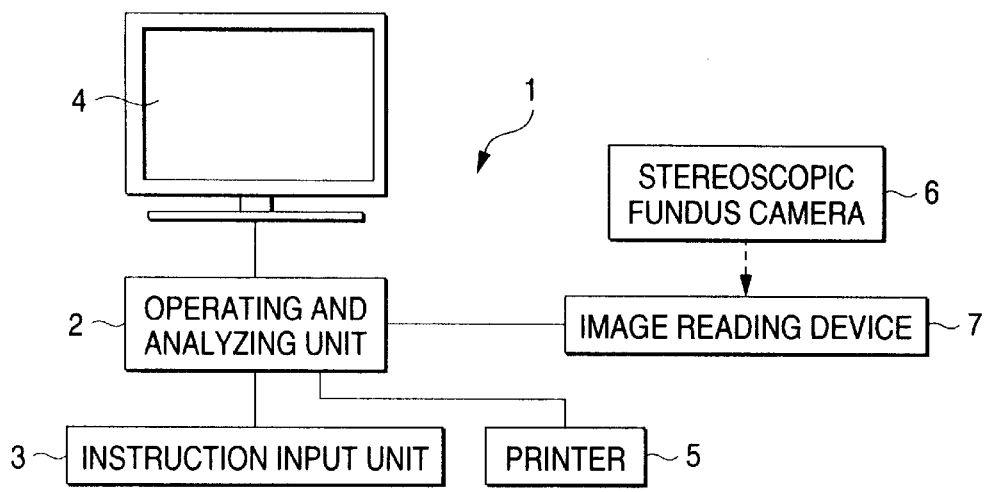
FIG. 1 is a schematic diagram of a fundus measuring apparatus in accordance with an embodiment.

Referring now to the drawings, a description will be given of an embodiment of the present invention. FIG. 1 is a schematic diagram of a fundus measuring apparatus in accordance with the embodiment.

A fundus measuring apparatus 1 includes an operating and analyzing unit 2; an instruction input unit 3 such as a keyboard and/or a mouse; a display 4 for displaying images of a fundus, results of measurement, and the like; a printer 5 for printing out; and an image reading device 7 serving as an image input unit. The image reading device 7 reads a pair of left and right stereoscopic images of the fundus photographed by a stereoscopic fundus camera 6, and inputs the read images to the operating and analyzing unit 2. As the measuring apparatus 1, it is possible to use a commercially available personal computer and its peripheral equipment. That is, a program for measuring a three-dimensional configuration of a fundus (described later) can be installed from a recording medium storing therein the program to the commercially available personal computer, etc. so that the commercially available personal computer, etc. is operable.

The stereoscopic fundus camera 6 divides a bundle of rays reflected from the fundus into two bundles of rays by means of a two-hole diaphragm so as to obtain a pair of left and right stereoscopic images of the fundus. As the stereoscopic fundus camera 6, a type is known in which images are photographed on a slide film and a type is known in which images are captured by a CCD camera. In the former type, the stereoscopic images of the fundus photographed by the fundus camera 6 are converted to digital image data by the image reading device 7, and are inputted to the operating and analyzing unit 2. In the latter type, the images of the fundus are stored in the memory or the like of the fundus camera 6 as still images, and can then be inputted directly or via a recording medium such as a floppy disc to the operating and analyzing unit 2.

Figure 2:
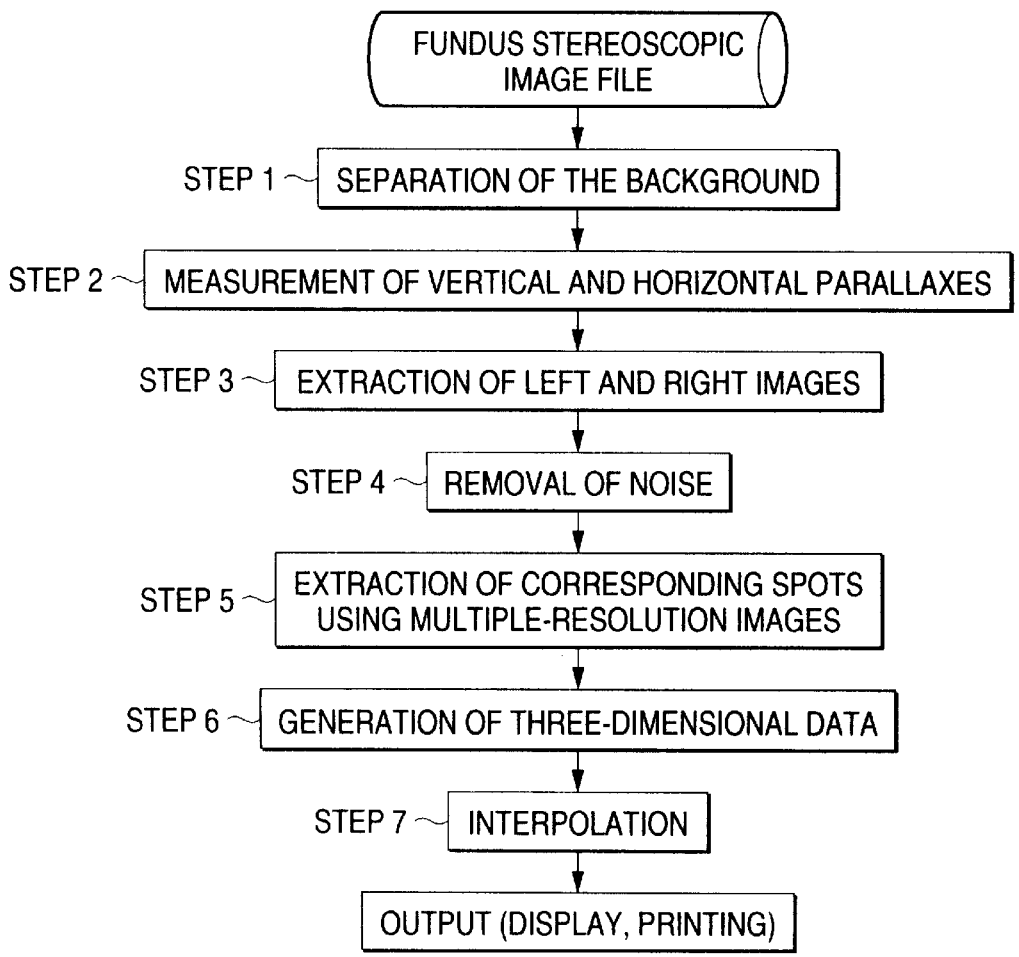
FIG. 2 is a flowchart illustrating the procedure of measurement of a three-dimensional configuration of the fundus.

FIG. 2 is a flowchart illustrating the procedure of measurement of the three-dimensional configuration of the fundus by the operating and analyzing unit 2. Hereafter, a description will be given of the measurement of the three-dimensional configuration of the fundus.

Figure 3:
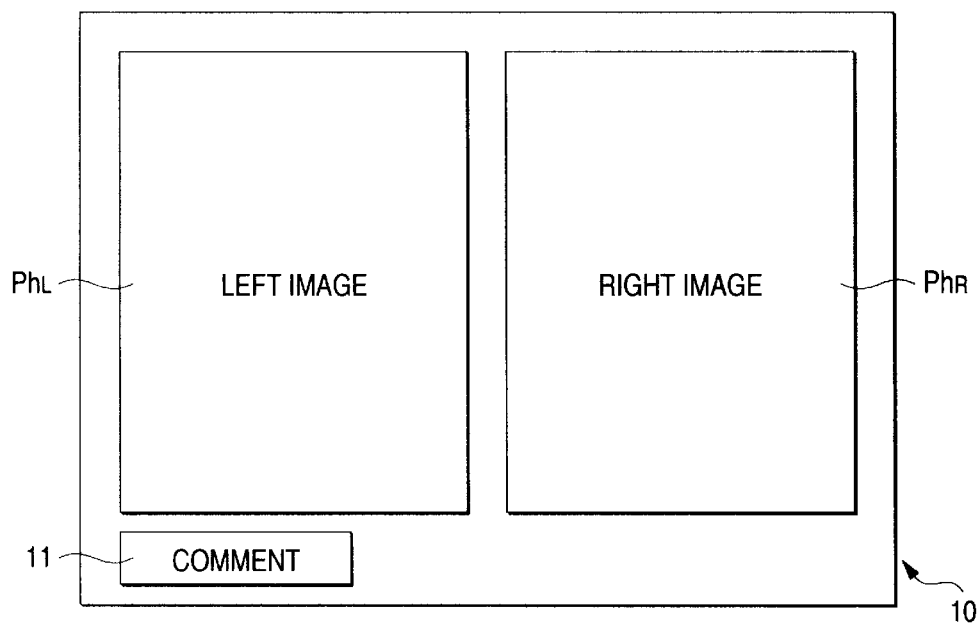
FIG. 3 is a diagram illustrating the arrangement of stereoscopic images of the fundus.

The images of the fundus of a subject eye photographed by the fundus camera 6 are obtained as a stereoscopic picture 10 of the fundus in which a left image $Ph_L$ and a right image $Ph_R$ are juxtaposed left and right (see FIG. 3). A comment area 11 is provided on the stereoscopic picture 10 of the fundus, so that a comment on the date of photographing and the like can be written thereon.

First, the stereoscopic picture 10 of the fundus is read by the image reading device 7. The stereoscopic picture 10 of the fundus which has been read by the image reading device 7 is converted to digital image data, and is inputted to the operating and analyzing unit 2 as a stereoscopic image file. Digitized stereoscopic image data 20 is composed of a set of pixels in which the density (luminance) of each spot is digitized, and is digitized on a scale of 256 ranging from 0 to 255, for example. By operating the instruction input unit 3, the operator instructs the operating and analyzing unit 2 to execute a program for measuring the three-dimensional configuration of the fundus. The operating and analyzing unit 2 measures the three-dimensional configuration of the fundus on the basis of the stereoscopic images of the fundus through the following steps.

Figure 4:
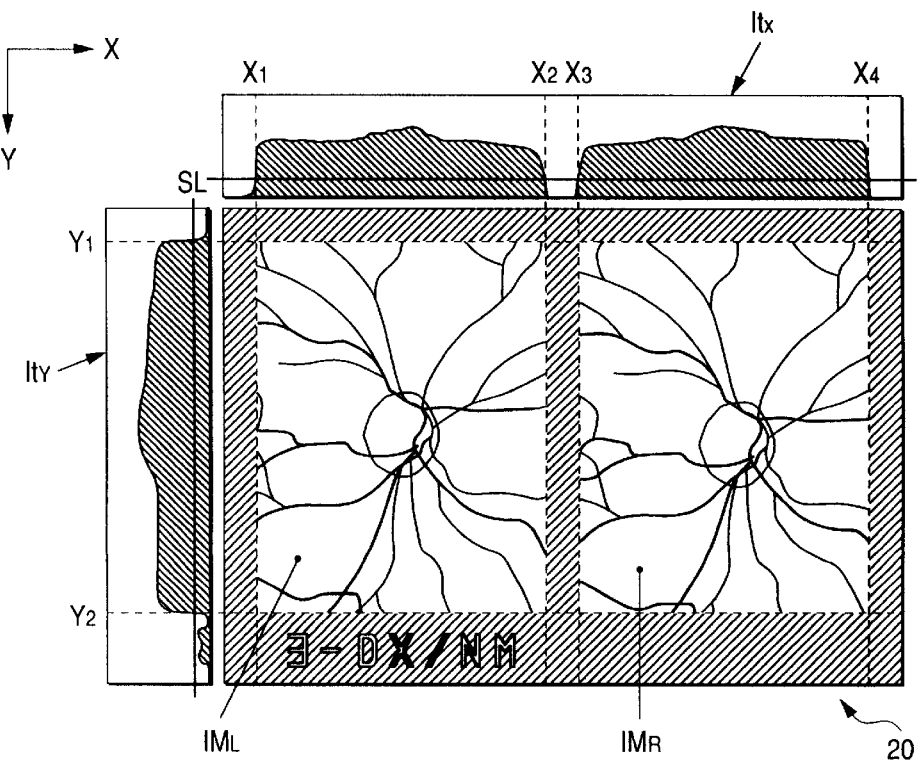
FIG. 4 is an explanatory diagram explaining background separation processing.

In Step 1, background separating processing is effected for separating and recognizing image portions and portions other than the same. Specifically, as shown in FIG. 4, after integration processing of the density values is performed with respect to the respective X and Y directions (horizontal and vertical directions) of the inputted image data, a threshold SL is provided for the integral value obtained, and a portion of a density value higher than this threshold value SL is recognized as an image portion. Although the threshold value SL can be set in advance, in this embodiment geometric value which is obtained by the following formula on the basis of a maximum value and a minimum value of the integral value is set as the threshold value SL independently for each integral value data.

Threshold value $SL=[\{\text{maximum value}-\text{minimum value}\}/4]+(\text{minimum value})$ If it is assumed that the coordinates of each point of intersection of the threshold value SL with respect to an integral value $It_x$ in the X direction and an integral value $It_y$ in the Y direction are X1, X2, X3, X4, Y1, and Y2, a rectangular form divided by X1, X2, Y1, and Y2 becomes a left fundus image $IM_L$, and a rectangular form divided by X3, X4, Y1, and Y2 becomes a right fundus image $IM_L$.

In Step 2, parallaxes (deviations of the images) due to the refractive error and the like of the photographed eye are measured. A vertical parallax due to the effect of the photographing optical system of the fundus camera 6 and a horizontal parallax due to the refractive error of the photographed eye occur in the left and right images obtained by the background separation. In the measurement of the three-dimensional configuration, it is necessary to correct parameters of its computational formula, so that the parallaxes are measured in advance. In addition, if the vertical and horizontal parallaxes can be known prior to the extraction of corresponding spots in Step 5 which will be described later, the point of a 0 parallax can be set as the initial value of the search of the corresponding spot (the corresponding spot can be searched upon shifting of the parallax), and a portion where the corresponding spot does not exist in the peripheral portion of the image can be excluded from the extraction of the corresponding spot. The measurement of the parallaxes is effected as follows.

First, integration processing is effected in the respective X and Y directions with respect to the density information on the left and right images $IM_L$ and $IM_R$ recognized in Step 1 so as to determine integral values. To prevent the measurement of the horizontal parallax from being affected by the disc, the integration processing in the Y direction is effected on the basis of the peripheral distribution excluding the central portion of the image (the cup of the disc). Specifically, only an upper one-third region and a lower one-third region of each of the left and right images $IM_L$ and $IM_R$ are subjected to integration processing so as to obtain integral values. On the other hand, since the measurement of the vertical parallax (integration in the X direction) uses the disc as a reference, all regions including the central portion is subjected to integration processing in the X direction.

Figure 5:
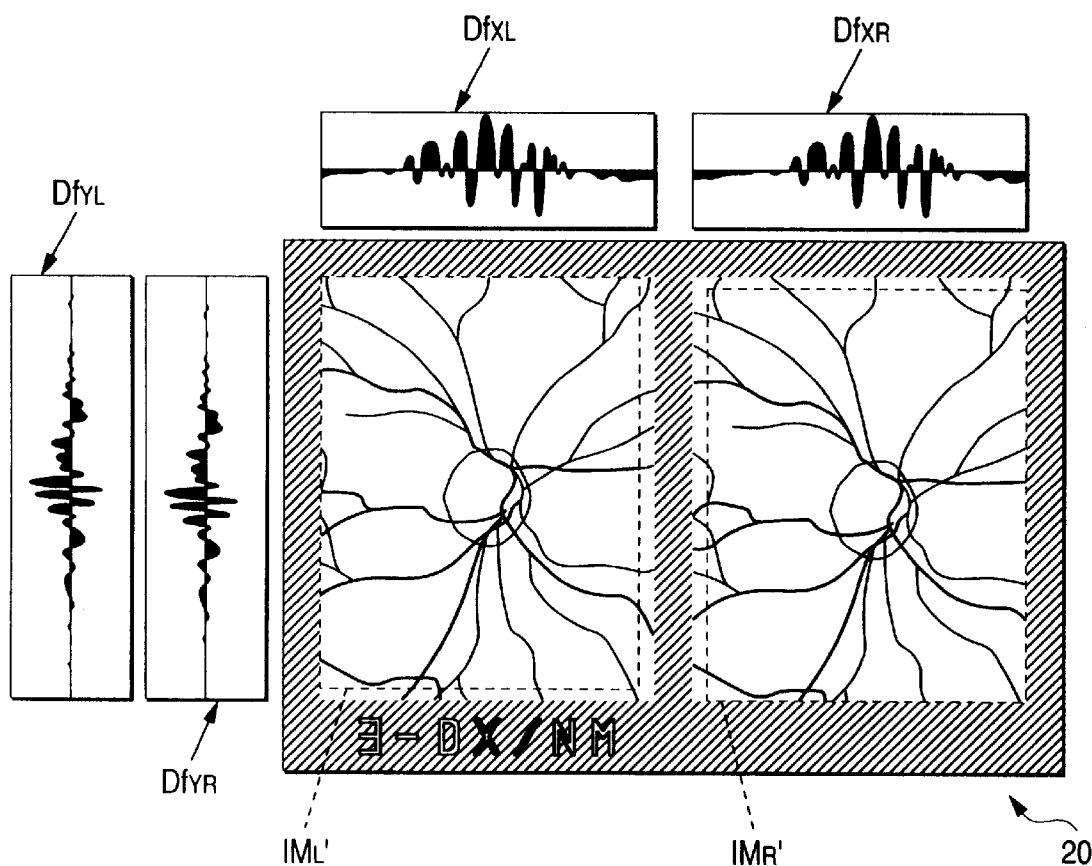
FIG. 5 is an explanatory diagram explaining measurement processing of vertical and horizontal parallaxes.

After the respective integral values have been obtained, differential processing is effected with respect to each of the integral values so as to obtain differential values. As shown in FIG. 5, the differential values of the left and right images $IM_L$ and $IM_R$ are respectively set as $Df_{XL}$, $Df_{XR}$, $Df_{YL}$, and $Df_{YR}$.

After the differential values $Df_{XL}$, $Df_{XR}$, $Df_{YL}$, and $Df_{YR}$ in the X and Y directions have been determined, maximum cross correlation values of the differential values in the vertical and horizontal directions are respectively obtained from these waveforms, and parallaxes (amounts of deviations of the images) in the vertical and horizontal directions are obtained on the basis of these maximum cross correlation values (this method is generally known as the cross correlation coefficient method). In the measurement of the parallax, attention is focused on not the structure of a large region which is dominated by the illuminance distribution and the reflectivity of the fundus but the structure based on the blood vessels and the like; therefore, by using the waveforms of such differential values, the characteristic structure of the blood vessels and the like can be accurately recognized even in the case of images of the fundus with poor contrast. In addition, since the vertical and horizontal parallaxes are measured independently of each other, the amount of calculation can be reduced as compared with the case in which the parallaxes are determined two-dimensionally, thereby making it possible to reduce the processing time.

In Step 3, processing is effected for extracting left and right image regions which are to be used in the extraction processing of corresponding spots in the subsequent Step 5. Specifically, the Step 3 excludes those portions which have been photographed only in the left image $IM_L$ or the right image $IM_R$ on the basis of the parallaxes (amounts of deviations of the images) in the vertical and horizontal directions obtained in Step 2, thereby extracting a left image region $IM_L'$ and a right image region $IM_R'$ to be used in the subsequent extraction processing of corresponding spots so as to correspond to each other. By extracting the left and right images in which no effect of the parallaxes remains, the extraction of corresponding spots can be facilitated.

In Step 4, to reduce noise superposed on the extracted left and right images $IM_L'$ and $IM_R'$, noise removal processing is effected by means of a noise removing filter such as a median filter (intermediate value filter) or the like.

In Step 5, with respect to the left and right images $IM_L'$ and $IM_R'$ subjected to extraction processing, a plurality of left and right images whose resolutions are consecutively lowered (hereafter referred to as multiple-resolution images) are prepared, and extraction processing of corresponding spots is effected on the basis of these images.

Figure 6:
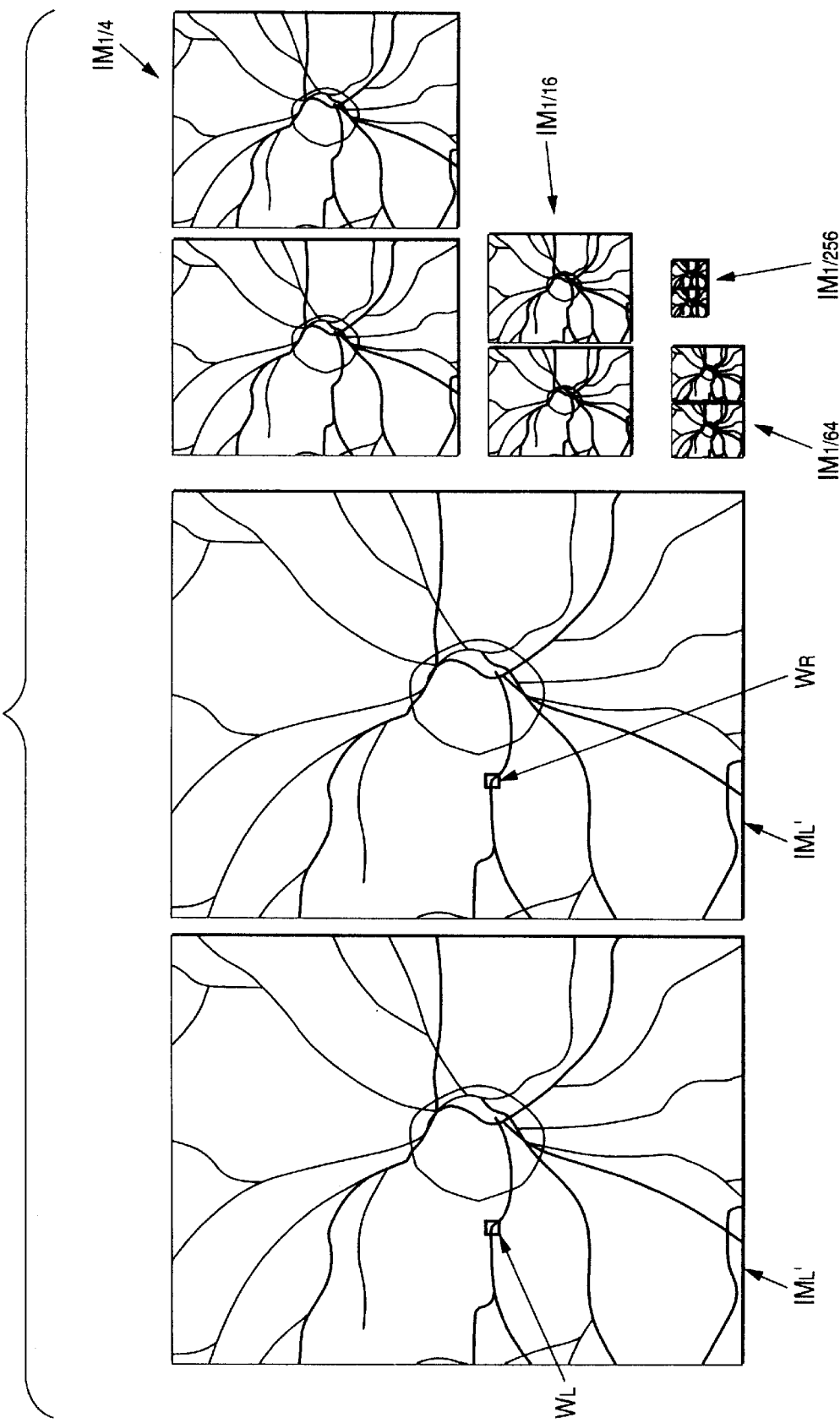
FIG. 6 is an explanatory diagram explaining corresponding-spot extraction processing using multiple-resolution images.

First, left and right images with reduced resolutions are respectively prepared with respect to the extracted left and right images $IM_L'$ and $IM_R'$. These images are, for example, a left-and-right image $IM_{1/4}$ in which the resolution of one line is reduced to half, a left-and-right image $IM_{1/16}$ in which the resolution of one line is further reduced to half of it, a left-and-right image $IM_{1/64}$ in which the resolution of one line is still further reduced to half of it, and a left-and-right image $IM_{1/256}$ in which the resolution of one line is still further reduced to half of it (see FIG. 6).

After preparation of the multiple-resolution images, extraction of corresponding spots is first effected with respect to the left-and-right image $IM_{1/256}$ having the lowest resolution. As for the method of extracting the corresponding spots at this time, a small region (hereafter referred to as a window) $W_L$ comprising a specific pixel and its neighboring pixels is set in the left image, and a window $W_R$ of the same size is moved in the horizontal direction of the right image to search for a place which is the best in conformity therewith. The region where the window $W_R$ is moved may not be an entire region, and the window $W_R$ may be moved only by the width where the corresponding spot is estimated to be present. In addition, as for the vertical direction, the search can be omitted by eliminating the vertical parallax in advance. Thus, the extraction of the corresponding spots is first effected with respect to the image $IM_{1/256}$; however, since the number of the pixels is only 1/256 of that of the original images $IM_L'$ and $IM_R'$, the same region can be searched with very short processing time.

Subsequently, extraction of the corresponding spots is effected with respect to the image $IM_{1/64}$ with the next lowest resolution. At this time, corresponding-spot position information obtained from the image $IM_{1/256}$ is fed back. That is, since the positional relationship between the image $IM_{l/256}$ and the image $IM_{1/64}$ can be made to correspond to each other on the basis of the magnification of the resolution, the extraction of corresponding spots in the image $IM_{1/64}$ is carried out such that a corresponding region to which the window $W_R$ corresponds is specified on the basis of the corresponding-spot position information obtained from the image $IM_{1/256}$, and then search is performed within a region of a predetermined width (the width where the corresponding spot is estimated to be present) including that corresponding region and its neighboring portion.

By a similar method, the extraction of corresponding spots is consecutively effected with respect to the image $IM_{1/16}$, the image $IM_{1/4}$, and the original images $IM_L'$ and $IM_R'$. As the corresponding-spot position information is thus consecutively fed back to images of higher resolution, and the extraction of corresponding spots is effected in narrow search regions, the same region can be searched in a short time in a total as compared with the case where the search is effected by using the images $IM_L'$ and $IM_R'$ alone.

In Step 6, height information is calculated on the basis of the corresponding-spot information extracted in Step 5 to generate three-dimensional data. A known collinear conditional expression can be used in the generation of the three-dimensional data, and the magnification affecting the refractive power of the photographed eye is corrected in the parallax information obtained in Step 2 to obtain actual three-dimensional data. The magnification for this correction can be easily obtained if a table concerning the relationship between the parallax (amount of deviation) and the correction magnification is stored in advance.

In the interpolation processing in Step 7, interpolation is effected with respect to the three-dimensional data generated in Step 6, and information is rearranged as the height data in lattice coordinates. By effecting interpolation processing, it is possible to prepare smoother three-dimensional graphics, an easy-to-understand contour map, a three-dimensional bird's-eye view, and so on.

After the three-dimensional configuration of the fundus is measured as described above, three-dimensional graphics and an orthogonal projection drawing of the fundus are displayed on the display 4. Further, if the operator commands the execution of a program on the analysis of the optic disc through the instruction input unit 3, the operating and analyzing unit 2 performs its analysis processing on the basis of the three-dimensional configuration data, and the results of analysis are displayed on the display 4.

As described above, in accordance with the present invention, the measurement of a three-dimensional configuration of the fundus can be effected accurately in a short processing time on the basis of stereoscopic images of the fundus.

What is claimed is:

1. A fundus measuring apparatus for measuring a three-dimensional configuration of a fundus on the basis of a stereoscopic image of the fundus, the apparatus comprising:

input means for inputting the stereoscopic image of the fundus;

image extracting means for extracting left and right images from the stereoscopic image of the fundus thus inputted by the input means;

wherein the image extracting means includes:

integration means for integrating horizontal and vertical density information on the stereoscopic image of the fundus thus inputted by the input means to obtain integral values;

threshold setting means for setting at least one threshold for the integral values thus obtained by the integration means; and background separating means for separating and extracting the left and right images from a background using coordinates obtained on the basis of the integral values and the at least one threshold value thus set by the threshold setting means; and three-dimensional configuration generating means for generating a three-dimensional configuration of the fundus on the basis of the left and right images thus extracted by the image extracting means.

2. The fundus measuring apparatus according to claim 1, wherein the image extracting means includes image separating means for excluding an image region which does not exist commonly on the left and right images.

3. The fundus measuring apparatus according to claim 1, wherein the input means is equipped with a fundus camera for photographing the stereoscopic image of the fundus.

4. The fundus measuring apparatus according to claim 1, further comprising:

output means for visually outputting the three-dimensional configuration of the fundus thus generated by the three-dimensional configuration generating means.

5. A fundus measuring apparatus for measuring a three-dimensional configuration of a fundus on the basis of a stereoscopic image of the fundus, the apparatus comprising:

input means for inputting the stereoscopic image of the fundus;

image extracting means for extracting left and right images from the stereoscopic image of the fundus thus inputted by the input means on the basis of a parallax;

wherein the image extracting means includes:

integration means for integrating at least one of horizontal and vertical density information on the stereoscopic image of the fundus thus inputted by the input means to obtain integral data;

differential means for differentiating the integral data thus obtained by integration means to obtain differential data; and parallax measuring means for obtaining the parallax on the basis of the differential data thus obtained by the differential means; and three-dimensional configuration generating means for generating a three-dimensional configuration of the fundus on the basis of the left and right images thus extracted by the image extracting means.

6. The fundus measuring apparatus according to claim 5, wherein the parallax measuring means obtains the parallax on the basis of maximum cross correlation values of the differential data obtained by the differential means.

7. The fundus measuring apparatus according to claim 5, wherein the image extracting means includes image separating means for excluding an image region which does not exist commonly on the left and right images.

8. The fundus measuring apparatus according to claim 5, wherein the input means is equipped with a fundus camera for photographing the stereoscopic image of the fundus.

9. The fundus measuring apparatus according to claim 5, further comprising output means for visually outputting the three-dimensional configuration of the fundus thus generated by the three-dimensional configuration generating means.

10. A fundus measuring apparatus for measuring a three-dimensional configuration of a fundus on the basis of a stereoscopic image of the fundus, the apparatus comprising:

input means for inputting the stereoscopic image of the fundus;

image extracting means for extracting left and right images from the stereoscopic image of the fundus thus inputted by the input means;

corresponding spots extracting means for generating multiple-resolution images whose resolutions are consecutively lowered with respect to the left and right images extracted by the image extracting means, and extracting corresponding spots from the left and right images using the multiple-resolution images in order starting from the lowest one of the multiple-resolution images; and three-dimensional configuration generating means for generating a three-dimensional configuration of the fundus on the basis of the left and right images thus extracted by the image extracting means and the corresponding spots thus obtained by the corresponding spots extracting means.

11. The fundus measuring apparatus according to claim 10, wherein the image extracting means includes image separating means for excluding an image region which does not exist commonly on the left and right images.

12. The fundus measuring apparatus according to claim 10, wherein the input means is equipped with a fundus camera for photographing the stereoscopic image of the fundus.

13. The fundus measuring apparatus according to claim 10, further comprising output means for visually outputting the three-dimensional configuration of the fundus thus generated by the three-dimensional configuration generating means.

14. A recording medium storing therein a program that is to be executed by an operating and analyzing unit to measure a three-dimensional configuration of a fundus on the basis of a stereoscopic image of the fundus, the program comprising:

an image extracting step of extracting left and right images from an inputted stereoscopic image of a fundus;

wherein the image extracting step includes the steps of:

integrating horizontal and vertical density information on the inputted stereoscopic image of the fundus to obtain integral values;

setting at least one threshold for the integral values thus obtained by the integrating step; and separating and extracting the left and right images from a background using coordinates obtained on the basis of the integral values and the at least one threshold value thus set by the setting step; and a three-dimensional configuration generating step of generating a three-dimensional configuration of the fundus on the basis of the left and right images thus extracted by the image extracting step.

15. The recording medium according to claim 14, wherein the image extracting step includes an image separating step of excluding an image region which does not exist commonly on the left and right images.

16. A recording medium storing therein a program that is to be executed by an operating and analyzing unit to measure a three-dimensional configuration of a fundus on the basis of a stereoscopic image of the fundus, the program comprising:

an image extracting step of extracting left and right images from an inputted stereoscopic image of a fundus on the basis of a parallax, wherein the image extracting step includes the steps of:

integrating at least one of horizontal and vertical density information on the inputted stereoscopic image of the fundus to obtain integral data;

differentiating the integral data thus obtained by the integrating step to obtain differential data; and obtaining the parallax on the basis of the differential data thus obtained by the differential step; and a three-dimensional configuration generating step of generating a three-dimensional configuration of the fundus on the basis of the left and right images thus extracted by the image extracting step.

17. The recording medium according to claim 16, wherein the image extracting step includes an image separating step of excluding an image region which does not exist commonly on the left and right images.

18. A recording medium storing therein a program that is to be executed by an operating and analyzing unit to measure a three-dimensional configuration of a fundus on the basis of a stereoscopic image of the fundus, the program comprising:

an image extracting step of extracting left and right images from an inputted stereoscopic image of a fundus;

a corresponding spots extracting step of generating multiple-resolution images whose resolutions are consecutively lowered with respect to the left and right images extracted by the image extracting step, and extracting corresponding spots from the left and right images using the multiple-resolution images in order starting from the lowest one of the multiple resolution images; and a three-dimensional configuration generating step of generating a three-dimensional configuration of the fundus on the basis of the left and right images thus extracted and the corresponding spots thus obtained by the corresponding spots extracting step.

19. The recording medium according to claim 18, wherein the image extracting step includes an image separating step of excluding an image region which does not exist commonly on the left and right images.

20. A fundus measuring apparatus for measuring a three-dimensional configuration of a fundus on the basis of a stereoscopic image of the fundus, the apparatus having an operating and analyzing unit storing therein a fundus measuring program comprising steps of:

integrating at least one of horizontal and vertical density information on an inputted stereoscopic image of a fundus to obtain integral data;

differentiating the integral data thus obtained by the integrating step to obtain differential data;

obtaining a parallax on the basis of the differential data thus obtained by the differential step;

extracting left and right images from the stereoscopic image on the basis of the parallax; and obtaining a height of each part of the fundus from the left and right images thus extracted to generate a three-dimensional configuration of the fundus.

21. A fundus measuring apparatus for measuring a three-dimensional configuration of a fundus on the basis of a stereoscopic image of the fundus, the apparatus having an operating and analyzing unit storing therein a fundus measuring program comprising steps of:

extracting left and right images from an inputted stereoscopic image of a fundus;

generating multiple-resolution images whose resolutions are consecutively lowered with respect to the left and right images thus extracted, and extracting corresponding spots from the right and left images using the multiple-resolution images in order starting from the lowest one of the multiple-resolution images; and generating a three-dimensional configuration of the fundus on the basis of the corresponding spots thus obtained.

22. A fundus measuring apparatus for measuring a three-dimensional configuration of a fundus on the basis of a stereoscopic image of the fundus, the apparatus having an operating and analyzing unit storing therein a fundus measuring program comprising the steps of:

integrating horizontal and vertical density information on an inputted stereoscopic image of a fundus to obtain integral values;

setting at least one threshold value for the integral values thus obtained by the integrating step;

separating and extracting left and right images from a background using coordinates, obtained on the basis of the integral values and the at least one threshold value thus set by the setting step; and obtaining a height of each part of the fundus from the left and right images thus extracted to generate a three-dimensional configuration of the fundus.

* * * * *